United States Patent [19]

Moilliet et al.

[11] Patent Number: 5,212,301

[45] Date of Patent: May 18, 1993

[54] SUBSTITUTED FLUOROBENZENES

[75] Inventors: John S. Moilliet, Bury; Richard D. Chambers, Whitesmocks; Michael H. Rock, Bourneville, all of England

[73] Assignee: Imperial Chemical Industries PLC, London, England

[21] Appl. No.: 880,419

[22] Filed: May 8, 1992

[30] Foreign Application Priority Data

May 10, 1991 [GB] United Kingdom ................ 9110181

[51] Int. Cl.$^5$ .................. C07D 295/06; C07D 291/08; C07D 223/14; C07C 65/105; C07C 65/21
[52] U.S. Cl. .................................. 540/450; 540/473; 540/545; 540/552; 540/567; 540/568; 540/576; 540/593; 544/2; 544/3; 544/5; 544/48; 544/47; 544/65; 544/63; 544/66; 546/112; 546/114; 546/115; 546/122; 548/122; 548/123; 548/124; 548/126; 548/950; 548/951; 558/62; 558/303; 560/8; 562/125; 562/126; 562/405; 562/840; 568/808; 568/812; 568/929; 568/936; 570/141; 570/143; 570/144; 570/147

[58] Field of Search ............... 570/141, 143, 144, 147; 540/450, 473, 545, 552, 567, 568, 576, 593; 544/2, 3, 5, 48, 65, 66, 47, 63; 546/112, 114, 115, 122; 560/8; 558/62, 303; 562/125, 126, 405, 840, 808, 812, 929, 936

[56] References Cited

PUBLICATIONS

Morrison & Boyd, *Organic Chemistry*, 4th ed. (596–598), 1975.
*The Chemistry of halides, pseudo-halides & azides* (1983). pp. 448–449.

*Primary Examiner*—Marianne M. Cintins
*Assistant Examiner*—Kimberly J. Kestler
*Attorney, Agent, or Firm*—Cushman, Darby & Cushman

[57] ABSTRACT

Introduction of a fluoro substituent into an aromatic ring adjacent an electron donating group is difficult producing mixed isomers and low yields of desired products.

A process for the introduction of a fluoro substituent into a substantially adjacent position to an electron-donating group into an aromatic compound in high yield is disclosed.

The fluoroaromatic compounds are useful as synthetic intermediates for example in the manufacture of agrochemicals, pharmaceuticals and dyestuffs.

6 Claims, No Drawings

SUBSTITUTED FLUOROBENZENES

This invention relates to a process for fluorinating 4-halo aromatic compounds specifically in the 3-position in high yield.

Introduction of a fluoro substituent into an aromatic ring adjacent an electron donating group is difficult, direct fluorination processes using fluorine produces mixed isomers i.e. fluorination is not regio-specific and low yields of desired products are obtained.

We have now found a process whereby a fluoro substituent can be introduced substantially adjacent an electron donating group in an aromatic ring.

According to the present invention there is provided a process for the preparation of a 3-fluoroaromatic compound by reacting an aromatic compound which carries an electron-withdrawing group in the 1-position and an electron-donating group in the 4-position with a gas comprising a mixture of fluorine and an inert gas containing up to 50% fluorine by volume.

It is preferred that the 3-fluoroaromatic compound is of Formula (1):

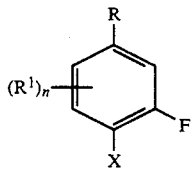

Formula 1 wherein
R is an electron withdrawing group;
X is an electron donating group;
$R^1$ is any substituent which does not interfere with fluorination, or two $R^1$ groups attached to adjacent carbon atoms together with these carbon atoms form a second ring; and
n is from 0 to 3.

The electron withdrawing group represented by R is preferably selected from $-CY_3$, $-SO_2Y^1$, $-COY^2$ and $-CN$ in which
Y is selected from $-F$ and $-Cl$;
$Y^1$ is selected from $-F$, $-Cl$, $-Br$, $-NH_2$, $-NH(C_{1-4}\text{-alkyl})$ and $N(C_{1-4}\text{-alkyl})_2$; and
$Y^2$ is selected from $-H$, $-F$, $-CL$, $-Br$, $-C_{1-4}\text{-alkyl}$, $-OH$ and $-OC_{1-4}\text{-alkyl}$.

The electron donating group may donate electrons via an inductive or a mesomeric effect or by a combination of the two effects.

The electron donating group represented by X is preferably halogen, more preferably $-F$ or $-Cl$.

The group, or where n > 1 the groups, represented by $R^1$ may independently be any of the groups defined above for R and X which does not interfere with the fluorination reaction and is preferably selected from $C_{1-6}$-alkyl, $C_{1-6}$-alkoxy, $NH_2$, $NH(C_{1-6}\text{-alkyl})$, $N(C_{1-6}\text{-alkyl})_2$, SH and $SC_{1-6}$-alkyl. Any of the groups represented by R and $R^1$ may themselves undergo fluorination during the process.

When two $R^1$ groups in the 5- and 6-positions of the benzene ring are combined to form a second ring this may be a 5- or 6-membered carbocyclic or heterocyclic ring fused to the benzene ring. Examples of compounds where two such $R^1$ groups are combined in this way are naphthalene, quinoline, benzopyran, benzothiophen, benzofuran, benzopyrrole and benzopyrrolidine analogues of the compound of Formula (1).

It is preferred that n is from 0 to 2, especially 0 or 1.

The preferred compound of Formula 1 may be derived from a compound of Formula (2)

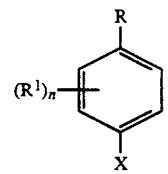

Formula 2 wherein: R, X, $R^1$ and n are as hereinbefore defined.

The process is preferably performed by reacting the compound of Formula (2) neat or in a suitable reaction medium with the aforementioned mixture of gases. The concentration of fluorine in inert gas is preferably from 1% to 50% by volume, more preferably from 2% to 30% and especially preferably from 5% to 15%. It is preferred that the fluorine gas is diluted with an inert gas such as nitrogen.

A suitable reaction medium is any liquid which does not react with the aromatic compound of Formula (2) or with the fluorine gas. A preferred reaction medium is a liquid such as a perhaloalkane for example carbon tetrachloride and 1,1,2-trichloro-1,2,2-trifluoro ethane, or a perhaloacetic acid for example trifluoroacetic acid or trichloroacetic acid, or acetonitrile or a mixture thereof. The reaction medium is preferably acetonitrile or trifluoroacetic acid.

The process may be carried out at a temperature from $-40°$ C. to $25°$ C., preferably from $-30°$ C. to $15°$ C. It is preferred that the process in a liquid such as acetonitrile is carried out at a temperature from $-35°$ C. to $-5°$ C. and more preferably at temperatures from $-30°$ C. to $-15°$ C. It is preferred that the process in a liquid such as trifluoroacetic acid is carried out at a temperature from $-5°$ C. to $25°$ C., more preferably at a temperature from $0°$ C. to $20°$ C., and especially preferably at a temperature from $5°$ C. to $15°$ C. Reactions in acetonitrile are at lower temperature than those in trifluoroacetic acid to minimise reaction of acetonitrile with the fluorine. Although the ratio of fluorine to the aromatic compound of Formula (2) may be varied within wide limits, it is preferred that the molar ratio of fluorine to aromatic compound of Formula (2) is from 1:1 to 2:1 in order to promote a good yield of the desired products and inhibit the formation of overfluorinated by-products.

When the fluorination reaction is substantially complete the product may be isolated in any convenient manner. For example the reaction mixture may be purged with nitrogen to remove residual fluorine and the reaction medium removed by distillation. Residual product may be purified by any convenient means such as distillation at atmospheric pressure or under reduced pressure or alternatively by recrystallisation from a suitable solvent if the product is a solid.

The 3-fluoroaromatic compounds of Formula (1) are useful as synthetic intermediates for example in the manufacture of agrochemicals, pharmaceuticals and dyestuffs.

the present process offers a convenient synthetic route to fluoroaromatic compounds having substitution patterns which are difficult to achieve by other routes.

Furthermore, the 3-fluoroaromatic compounds of Formula (1) in which X is halogen may be readily converted into 1-fluoro-2-haloaromatic compounds by removal of the group R using methods known in the art.

The invention is illustrated by the following examples.

EXAMPLE 1

A solution of 4-fluorobenzenesulphonyl chloride (0.015 mol) in acetonitrile (15 cm$^3$) was cooled to −30° C. under a flow of nitrogen. A 10% by volume mixture of fluorine (0.03 mol) in nitrogen was passed through the cooled solution at −30° C. When all the fluorine has been added the reaction mixture was warmed to ambient temperature under a flow of nitrogen. The reaction mixture was analysed by 19 F nmr and mass spectrometry using authentic samples as standards. From the analysis 95% of the 4-fluorobenzenesulphonyl chloride was converted to fluorinated product and this was 3,4-difluorobenzene sulphonyl chloride (100%).

EXAMPLE 2

The procedure of Example 1 was followed except that 4-fluorobenzoyl chloride (0.015 mol) was used in place of 4-fluorobenzene sulphonyl chloride and 0.015 mol instead of 0.03 mol of fluorine was used. 50% of the 4-fluorobenzoyl chloride was converted to fluorinated product comprising 3,4-difluorobenzoylchloride (>95%).

EXAMPLE 3

The procedure of Example 2 was followed except that 0.015 mol of 4-fluorobenzotrifluoride was used in place of the 4-fluorobenzene sulphonyl chloride. 65% of the 4-fluorobenzotrifluoride was converted to fluorinated product comprising 3,4-difluorobenzotrifluoride (>95%).

EXAMPLE 4

The procedure of Example 1 was followed except that 0.015 mol of 4-fluorobenzotrifluoride was used in place of the 4-fluorobenzene sulphonyl chloride. 90% of the 4-fluorobenzotrifluoride was converted to fluorinated product comprising 3,4-difluorobenzotrifluoride (>90%).

EXAMPLE 5

The procedure of Example 1 was followed except that 0.015 mol of 4-fluorobenzotrichloride was used in place of the 4-fluorobenzene sulphonyl chloride. 90% of the 4-fluorobenzotrichloride was converted to fluorinated product comprising 3,4-difluorobenzotrichloride (>90%) and small amounts of compounds containing a trifluoromethyl group.

EXAMPLE 6

The procedure of Example 2 was followed except that 0.015 mol of 4-fluoroacetophenone was used in place of the 4-fluorobenzene sulphonyl chloride. 70% of the 4-fluoroacetophenone was converted to fluorinated product comprising 3,4-difluoroacetophenone (>85%) and small amounts of compounds containing a trifluoromethyl group.

EXAMPLE 7

The procedure of Example 2 was followed except that 0.015 mol of 4-fluorobenzonitrile was used in place of the 4-fluorobenzene sulphonyl chloride. 70% of the 4-fluorobenzonitrile was converted to fluorinated product comprising 3,4-difluorobenzonitrile (>90%) and small amounts of compounds containing a trifluoromethyl group.

EXAMPLE 8

A solution of 4-fluorobenzoic acid (0.015 mol) in trifluoroacetic acid (15 parts) was cooled to 15° C. under a flow of nitrogen. A 10% by volume mixture of fluorine (0.03 mol) and nitrogen was passed through the solution at 15° C. When all the fluorine was added the reaction mixture was warmed to ambient temperature under a flow of nitrogen. 90% of the 4-fluorobenzoic acid was converted to fluorinated product and this was 3,4-difluorobenzoic acid (100%).

EXAMPLE 9

The procedure of Example 1 was followed except that 0.015 mol instead of 0.03 mol of fluorine was used. 50% of the 4-fluorobenzene sulphonyl chloride was converted to fluorinated product, and this was 3,4-difluorobenzenesulphonyl chloride (100%).

We claim:

1. A process for the preparation of a 3-fluoroaromatic compound by reacting an aromatic compound which carries an electron-withdrawing group in the 1-position and an electron-donating group in the 4-position with a gas comprising a mixture of fluorine and an inert gas containing up to 50% fluorine by volume.

2. A process according to claim 1 wherein the 3-fluoroaromatic compound is of Formula (1):

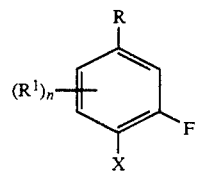

Formula 1 wherein
R is an electron withdrawing group;
X is an electron donating group;
R$^1$ is any substituent which does not interfere with fluorination, or two R$^1$ groups attached to adjacent carbon atoms together with these carbon atoms form a second ring; and
n is from 0 to 3.

3. A process according to claim 2 wherein in the compound of Formula (1)
R is —CY$_3$, —SO$_2$Y$^1$, —COY$^2$ or —CN,
in which
Y is —F or —Cl,
Y$^1$ is —F, —Cl, —Br, —NH$_2$, —NH(C$_{1-4}$-alkyl) or —N(C$_{1-4}$-alkyl)$_2$,
Y$^2$ is —H, —F, —Cl, —Br, —C$_{1-4}$-alkyl, —OH or —OC$_{1-4}$-alkyl;
X is halogen;
R$^1$ is —CY$_3$, —SO$_2$Y$^1$, —COY$^2$, —CN, C$_{1-6}$-alkyl, C$_{1-6}$-alkoxy, NH$_2$, NH(C$_{1-6}$-alkyl), N(C$_{1-6}$-alkyl)$_2$), SH or SC$_{1-6}$-alkyl, in which Y, Y$^1$ and Y$^2$ are as hereinbefore defined, or two R$^1$ groups attached to adjacent carbon atoms together with these carbon atoms form a second ring; and
n is from 0 to 3.

4. A process according to claim 2 or claim 3 wherein R is —SO$_2$Cl, —COCl, —CN, —CF$_3$, —CCl$_3$, —COCH$_3$ or —COOH;

X is —F or —Cl;

$R^1$ is —$CY_3$, —$SO_2Y^1$, —$COY^2$, —CN, $C_{1\text{-}6}$-alkyl, $C_{1\text{-}6}$-alkoxy, $NH_2$, $NH(C_{1\text{-}6}\text{-alkyl})$, $N(C_{1\text{-}6}\text{-alkyl})_2$), SH or $SC_{1\text{-}6}$-alkyl, in which Y is —F or —Cl, $Y^1$ is —F, —Cl, —Br, —$NH_2$, —$NH(C_{1\text{-}4}\text{-alkyl})$ or —$N(C_{1\text{-}4}\text{-alkyl})_2$, $Y^2$ is —H, —F, —Cl, —Br, —$C_{1\text{-}4}$-alkyl, —OH or —$OC_{1\text{-}4}$-alkyl, or two $R^1$ groups attached to adjacent carbon atoms together with these carbon atoms form a second ring; and n is from 0 to 2.

5. A process according to any one of claims 1 to 4 wherein the process is carried out at a temperature from −40° C. to 25° C.

6. A process according to any one of claims 1 to 5 wherein the molar ratio of fluorine to aromatic compound is from 1:1 to 2:1.

* * * * *